United States Patent [19]

Maillard et al.

[11] 4,423,056

[45] Dec. 27, 1983

[54] 5(AMINOMETHYL)-4,5,6,7-TETRAHYDRO[D]THIAZOLE CONTAINING COMPOSITIONS FOR AND MEDICAL USE IN TREATING CIRCULATORY INSUFFICIENCIES

[75] Inventors: Jacques G. Maillard, Versailles; Pierre P. A. Delaunay, Herblay; Jacky M. G. Legai, Palaiseau, all of France

[73] Assignee: Laboratoires Jacques Logeais, Issy-les-Moulineaux, France

[21] Appl. No.: 356,617

[22] Filed: Mar. 10, 1982

Related U.S. Application Data

[62] Division of Ser. No. 160,458, Jun. 18, 1980, Pat. No. 4,337,343.

[30] Foreign Application Priority Data

Jun. 20, 1979 [FR] France ............................ 79 15774

[51] Int. Cl.³ .......................................... A61K 31/425
[52] U.S. Cl. ................................................. 424/270
[58] Field of Search ........................................ 424/270

[56] References Cited

PUBLICATIONS

Yoshizaki et al., "J. Med. Chem." (1976), vol. 19, pp. 1138–1142.
Keck et al., "Drug Res.", 22, (1972), pp. 861–869.

Primary Examiner—Donald G. Daus
Assistant Examiner—D. B. Springer
Attorney, Agent, or Firm—Young & Thompson

[57] ABSTRACT

This invention relates to compounds of the formula (I):

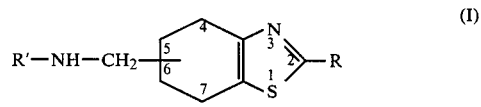

in which: R is selected from hydrogen and $C_{1-6}$alkyl and R' is selected from hydrogen and $C_{1-6}$alkyl; and their pharmaceutically acceptable acid addition salts.

Said compounds are therapeutically useful for the treatment of circulatory insufficiencies.

6 Claims, No Drawings

5(AMINOMETHYL)-4,5,6,7-TETRAHYDRO[D]-THIAZOLE CONTAINING COMPOSITIONS FOR AND MEDICAL USE IN TREATING CIRCULATORY INSUFFICIENCIES

This application is a division of application Ser. No. 160,458, filed June 18, 1980 now U.S. Pat. No. 4,337,343.

DESCRIPTION

This invention relates to amino benzothiazole derivatives, a process for their preparation and their therapeutical applications.

Applicant has previously disclosed in French Patent FR 7731891 aminobenzothiazole derivatives which have an useful activity on the central nervous system.

This invention relates to new amino benzothiazole derivatives which could be prepared only via an entirely different synthetic route and which, additionally, are applicable in a different therapeutic area.

Thus, this invention relates to compounds having the general formula (I):

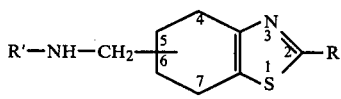

in which: R is hydrogen or $C_{1-6}$ alkyl, and R' is hydrogen or $C_{1-6}$ alkyl, and their pharmaceutically acceptable acid addition salts.

The addition salts may typically be those formed with hydrochloric, hydrobromic, sulfuric acids and the pharmaceutically acceptable organic acids.

This invention relates also to a process for the preparation of the compounds of the formula (I), comprising:

(a) reacting a bromo keto-ester of the formula (II):

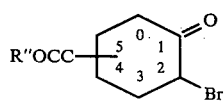

in which R'' is $C_{1-2}$ alkyl, with a thioamide of the formula

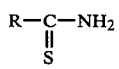

in which R is as previously defined, to give an ester of the formula (III):

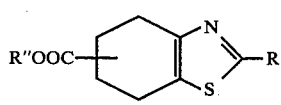

(b) reducing the ester of the formula (III) with lithium aluminum hydride to an alcohol of the formula (IV):

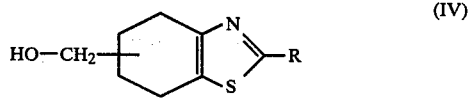

(c) converting the alcohol of the formula (IV), with p-toluenesulfonyl chloride, to the corresponding tosylate of the formula (V):

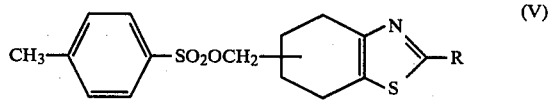

(d) reacting the tosylate of the formula (V) with an amine of the formula $R'—NH_2$ in which R' is as previously defined, to give an amine of the formula (I), and, if desired, (e) converting the amine of the formula (I) to a pharmaceutically acceptable acid addition salt.

Some of the bromo esters (II) used as starting materials are known compounds:

2-bromo-6-ethoxycarbonyl-cyclohexanone (J. E. BRENNER, J. Org. Chem., 1961, 26, 22), 2-bromo-4-ethoxycarbonyl-cyclohexanone (L. BERGER and co-workers, German Patent No. 2,214,501, Oct. 5, 1971, Chem. Abstr. 1973, 78, 29609b).

The other bromo keto-esters of the formula (II) are prepared in an analogous manner.

The reaction with a thioamide may be effected within a solvent such as an alcohol (ethanol, isopropanol) or dimethylformamide, at room temperature in the case of low molecular weight thioamides ($R=H$, $CH_3$) or with mild heating in the case of higher thioamides (40°–60° C.).

The resulting benzothiazole (III) may be isolated, after evaporating off the solvent, due to its slightly basic character (dissolution in aqueous acidic medium).

Step (b), comprising reducing ester (III) to an alcohol (IV) with lithium aluminum hydride, may be effected within ether or tetrahydrofuran, at room temperature (or preferably at a low temperature $<0°$ C. in the case of the derivatives in which $R=H$).

The alcohols (IV) may be isolated and purified according to usual techniques (distillation, crystallization), or directly converted to tosylates (V) with p-toluenesulfonyl chloride, in the presence of a tertiary base such as pyridine.

The tosylates (V) may be purified by crystallization or may be used crude for the reaction with amine $R'NH_2$. For this latter reaction, excess primary amine $R'NH_2$ is advantageously used within a solvent such as methanol or ethanol, in an autoclave and at a temperature of about 100° C.

The resulting amines (I) are obtained by evaporating off the solvent and are distilled under reduced pressure. These are strong bases, which are fairly readily converted to the carbonates on exposure to the air.

They are advantageously converted to salts, such as the hydrochlorides, by addition of a slight deficiency of anhydrous acid, within an inert solvent such as ether.

The following non-limiting Examples illustrate the present invention.

EXAMPLE 1

4-Aminomethyl-4,5,6,7-tetrahydro-benzo[d]thiazole and its hydrochloride (I, R=R'=H; substitution at 4-position)

(1)

4-Ethoxycarbonyl-4,5,6,7-tetrahydro-benzo[d]thiazole (III)

90 g (0.36 mole) 2-bromo-6-ethoxycarbonyl-cyclohexanone (II) are dissolved in 300 ml anhydrous ethanol containing 22 g (0.36 mole) thioformamide. After 60 hrs at room temperature and evaporation of the solvent, the residue is taken up into isopropyl oxide and extracted repeatedly with 2 N HCl. The acidic solution is made alkaline and the resulting oil is extracted with ether and is then distilled (b.p.$_{0.1}$=100)104° C. Yield=31%.

(2)

4-Hydroxymethyl-4,5,6,7-tetrahydro-benzo[d]thiazole (IV)

To a solution of 1.14 g (30 mmoles) of AlLiH$_4$ in 50 ml anhydrous tetrahydrofuran, cooled to −20° C. and maintained at that temperature, are slowly added 6.66 g (30 mmoles) of the above derivative (III) dissolved in 30 ml anhydrous THF. After 30 minutes at −20° C., excess AlLiH$_4$ is destroyed by addition of isopropanol at −20° C. followed by 5 ml saturated aqueous sodium chloride, and is then stirred for 2 hrs. The resulting precipitate is filtered off and washed with ethyl acetate; the filtrate is evaporated and the oily residue is taken up in the hot with hexane; product (IV) crystallizes on cooling. Yield: 70%. M.p.=74°-75° C.

(3)

4-Tosyloxymethyl-4,5,6,7-tetrahydrobenzo[d]thiazole (V)

9.95 g (52 mmoles) p-toluenesulfonyl chloride are added portionwise to a mixture of 8 g (47 mmoles) of the above derivative (IV) and 15 g anhydrous pyridine, while maintaining the temperature at 10° C. After stirring for 24 hrs at room temperature, the mixture is hydrolyzed and is then extracted with ethyl acetate. The combined organic phases are washed with water, dried and evaporated. The residual oil crystallizes slowly. The product is recristallyzed from boiling isopropyl oxide, on cooling. Yield: 72%. M.p.=64°-65° C.

(4) 4-Aminomethyl-4,5,6,7-tetrahydrobenzo[d]thiazole and its hydrochloride (I, R=R'=H)

A solution of 26 g (80 mmoles) of the above derivative (V) in 40 ml methanol is heated with 180 g ammonia, in an autoclave, for 5 hrs at 90° C. After evaporation of the solvent and addition of 3.8 g (96 mmoles) sodium hydroxide dissolved in 25 ml water, the resulting amine is extracted repeatedly with ether, dried and distilled. B.p.$_{0.1}$=97°-100° C. Yield=54%.

The amine (I, R=R'=H) is converted to the hydrochloride by addition of a slight deficiency of anhydrous HCl to a solution of the base in ether. Yield: 98%. M.p.=210° C.

EXAMPLE 2

4-(N-Methylaminomethyl)-4,5,6,7-tetrahydro-benzo[d]thiazole and its hydrochloride (I, R=H; R'=CH$_3$; substitution at 4-position)

30.4 g (93 mmoles) of derivative (V) described in Example 1 are stirred for 60 hrs at room temperature with a solution of 150 g methylamine in 150 ml water. The mixture is homogeneous after 48 hrs. The solution is evaporated to dryness; the residue is taken up into excess 2 N sodium hydroxide and extracted with methylene chloride. The oily residue obtained after evaporation of the solvent is distilled. B.p.$_{0.2}$=96°-99° C. Yield: 80%.

The amine is converted to the hydrochloride by addition of a slight deficiency of anhydrous HCl, in ether. Yield: 88%. M.p.=120° C. (dec.).

EXAMPLE 3

2-Methyl-4-aminomethyl-4,5,6,7-tetrahydro-benzo[d]thiazole and its hydrochloride (I, R=CH$_3$; R'=H; 4-substitution)

(1)

2-Methyl-4-ethoxycarbonyl-4,5,6,7-tetrahydrobenzo[d]thiazole (III)

This compound is prepared by action of thioacetamide on 2-bromo-6-carbethoxy-cyclohexanone (II), according to the process described in Example 1. B.p.$_{0.1}$=102°-105° C.

(2)

2-Methyl-4-hydroxymethyl-4,5,6,7-tetrahydrobenzo[d]thiazole (IV)

The compound is prepared by reduction of above derivative (III) with AlLiH$_4$, according to the process described in Example 1. B.p.$_{0.4}$=102°-106° C. Yield: 82%.

(3)

2-Methyl-4-tosyloxymethyl-4,5,6,7-tetrahydrobenzo[d]thiazole (V)

This compound is prepared by action of p-toluenesulfonyl chloride on above alcohol (IV), according to the process of Example 1. M.p.=97°-98° C. Yield: 89%.

(4)

2-Methyl-4-aminomethyl-4,5,6,7-tetrahydrobenzo[d]thiazole and its hydrochloride (I; R=CH$_3$; R'=H)

The compound is prepared by action of ammonia on the above tosylate (V), according to the process described in Example 1. B.p.$_{0.1}$=76°-78° C. Yield: 75%. (the base is rapidly carbonated in air).

The amine is converted to the hydrochloride with anhydrous HCl, in ether. M.p.=140° C. (dec.). Yield: 90%.

EXAMPLE 4

2-Methyl-4-(N-methylaminomethyl)-4,5,6,7-tetrahydro-benzo[d]thiazole and its hydrochloride (I; R=R'=CH$_3$; 4-substitution)

This compound is prepared from tosylate (V) described in Example 3, by action of a large excess of methylamine dissolved in methanol, at 130° C. in an autoclave. The amine is isolated according to the usual procedure, described in the preceding Examples. B.P.$_{0.5}$=98°-102° C. Yield: 38%.

The amine is converted to the hydrochloride with a slight deficiency of anhydrous HCl, dissolved in ether. M.p.=144° C. (dec.). Yield: 75%.

EXAMPLE 5

5-(N-Methylaminomethyl)-4,5,6,7-tetrahydro-benzo[d]thiazole and its hydrochloride (I; R=H; R'=CH$_3$; 5-substitution)

(1)

5-Methoxycarbonyl-4,5,6,7-tetrahydro-benzo[d]thiazole (III)

The compound is prepared by action of thioformamide on 2-bromo-5-methylcarbonyl cyclohexanone, as described in Example 1. B.p. 0.4=110°-120° C. Yield: 35.5%.

(2)

5-Hydroxymethyl-4,5,6,7-tetrahydro-benzo[d]thiazole (IV)

The compound is prepared by reduction of compound (III) obtained above with AlLiH$_4$, as described in Example 1. B.p.$_{0.6}$=138°-144° C. Yield=81%.

(3)

5-Tosyloxymethyl-4,5,6,7-tetrahydro-benzo[d]thiazole (V)

The compound is prepared from above derivative (IV) according to the procedure of Example 1. M.p.=87°-88° C. Yield: 70%.

(4)

5-(N-methylaminomethyl)-4,5,6,7-tetrahydrobenzo[d]thiazole and its hydrochloride (I; R=H; R'=CH$_3$)

The compound is prepared by action of methylamine dissolved in ethanol, on the above tosylate (IV), in an autoclave at 100° C. B.p.$_{0.5}$=115°-120° C. Yield: 82%. Hydrochloride: M.p.=201°-202° C. Yield: 82%.

EXAMPLE 6

2-Methyl-5-(N-methylaminomethyl)-4,5,6,7-tetrahydrobenzo[d]thiazole and its hydrochloride (I; R=R'=CH$_3$; substitution at 5-position)

(1)

2-Methyl-5-ethoxycarbonyl-4,5,6,7-tetrahydro-benzo[d]thiazole (III)

The compound is prepared by action of thioacetamide on 2-bromo-5-ethoxycarbonyl cyclohexanone (II), as described in Example 1. B.P.$_{0.4}$=116°-120° C.

(2)

2-Methyl-5-hydroxymethyl-4,5,6,7-tetrahydro-benzo[d]thiazole (IV)

The compound is prepared by reduction of the above derivative (III) with AlLiH$_4$, according to the procedure described in Example 1. B.p.$_{0.5}$=120°-140° C.

The crude product is purified by crystallization from carbon tetrachloride. M.p.=52°-55° C.

(3)

2-Methyl-5-tosyloxymethyl-4,5,6,7-tetrahydrobenzo[d]thiazole (V)

The compound is prepared by action of p-toluenesulfonyl chloride on the above alcohol (IV), according to the procedure described in Example 1. M.p.=105°-106° C. Yield: 74%.

(4)

2-Methyl-5-(N-methylaminomethyl)-4,5,6,7-tetrahydrobenzo[d]thiazole (I; R=R'=CH$_3$)

The compound is prepared by action of methylamine on the above tosylate (V) dissolved in methanol, in an autoclave at 100° C. B.P.$_{0.5}$=100°-110° C. Yield: 75%.

The amine is converted to the hydrochloride according to the procedure described in Example 1. M.p.=248°-250° C. (dec.). Yield; 80%.

EXAMPLE 7

2-Methyl-6-(N-methylaminomethyl)-4,5,6,7-tetrahydrobenzo[d]thiazole and its hydrochloride (I; R=R'=CH$_3$; substitution at 6-position)

(1)

2-Methyl-6-ethoxycarbonyl-4,5,6,7-tetrahydrobenzo[d]thiazole (III)

The compound is prepared by action of thioacetamide on 2-bromo-4-ethoxycarbonyl-cyclohexanone according to the procedure described in Example 1. B.p.$_{0.3}$=110°-120° C. Yield: 30%.

(2)

2-Methyl-6-hydroxymethyl-4,5,6,7-tetrahydrobenzo[d]thiazole (IV)

The compound is prepared by reduction of the above derivative (III) according to the procedure described in Example 1. B.p.$_{0.4}$=145°-155° C. M.p.=101°-102° C. Yield: 70%.

(3)

2-Methyl-6-tosyloxymethyl-4,5,6,7-tetrahydrobenzo[d]thiazole (V)

The compound is prepared by action of p-toluenesulfonyl chloride on the above derivative (IV) according to the procedure described in Example 1. M.p.=70°-71° C. Yield: 71%.

(4)

2-Methyl-6-(N-methylaminomethyl)-4,5,6,7-tetrahydrobenzo[d]thiazole and its hydrochloride (I; R=R'=CH$_3$)

The compound is prepared by action of methylamine dissolved in methanol, on the above tosylate (V), in an autoclave at 100° C. B.p.$_{0.3}$=105°-115° C. Yield: 83%.

The base is converted to the hydrochloride with a slight deficiency of HCl in anhydrous ether. M.p.=176°-178° C. Yield: 93%.

EXAMPLE 8

6-Aminomethyl-4,5,6,7-tetrahydro-benzo[d]thiazole and its hydrochloride (I; R=R'=H; 6-substitution)

(1)6-Ethoxycarbonyl-4,5,6,7-tetrahydro-benzo[d]thiazole (III)

The compound is obtained by action of thioformamide on 2-bromo-4-ethoxycarbonyl-cyclohexanone, according to the procedure described in Example 1. B.p.$_{0.2}$=105°-115° C. Yield: 27%.

(2)

6-Hydroxymethyl-4,5,6,7-tetrahydro-benzo[d]thiazole (IV)

The compound is prepared by reduction of the above derivative (III) according to the procedure described in Example 1. B.p.$_{.1}$=140°-150° C. Yield: 66%.

(3)
6-Tosyloxymethyl-4,5,6,7-tetrahydro-benzo[d]thiazole (V)

The compound is prepared from the above derivative (IV) according to the procedure described in Example 1. M.p.=90°–91° C. Yield: 64%.

(4) 6-Aminomethyl-4,5,6,7-tetrahydro-benzo[d]thiazole (I; R=R'=H)

The compound is prepared by action of ammonia on the above tosylate (V), in methanol, in a autoclave at 100° C. B.p.$_{0.5}$=100°–106° C. Yield: 42%.

Hydrochloride: M.p.=218°–219° C. Yield: 95%.

EXAMPLE 9

2-Ethyl-6-(N-ethylaminomethyl)-4,5,6,7-tetrahydrobenzo[d]thiazole and its hydrochloride (I; R=R'=C$_2$H$_5$; substitution at 6-position)

(1)
6-Ethoxycarbonyl-4,5,6,7-tetrahydro-benzo[d]thiazole (III)

The compound is prepared by action of thiopropionamide on 2-bromo-4-ethoxycarbonyl cyclohexanone within dimethyl formamide at room temperature. B.p.$_{0.2}$=112°–118° C. Yield: 42%.

(2)
2-Ethyl-6-hydroxymethyl-4,5,6,7-tetrahydro-benzo[d]thiazole (IV)

The compound is prepared by reduction of the above derivative (III) with AlLiH$_4$ within ether, at room temperature. B.p.$_{0.5}$=142°–144° C. Yield: 86%.

(3)
2-Ethyl-6-tosyloxymethyl-4,5,6,7-tetrahydrobenzo[d]thiazole (V)

The compound is prepared by action of p-toluenesulfonyl chloride on the above derivative (IV), according to the procedure described in Example 1. M.p.=54°–56° C. Yield: 65%.

(4)
2-Ethyl-6-(N-ethylaminomethyl)-4,5,6,7-tetrahydrobenzo[d]thiazole and its hydrochloride (I; R=R'=C$_2$H$_5$)

The compound is prepared by action of ethylamine in methanol solution of the above tosylate (V), in an autoclave at 90° C. B.p.$_{0.1}$=106°–109° C. Yield: 71%.

Hydrochloride: M.p.=187° C. Yield: 100%.

EXAMPLE 10

6-(N-n-Propylaminomethyl)-4,5,6,7-tetrahydro-benzo[d]thiazole and its hydrochloride (I; R=H; R'=nC$_3$H$_7$; substitution at 6-position)

The compound is prepared from the tosylate (V) described in Example 8, by action of a methanol solution of n-propylamine, in an autoclave at 90° C. B.p.$_{0.05}$=96°–100° C. Yield: 61%.

The base is converted to the hydrochloride with HCl dissolved in anhydrous ether. M.p.=166° C. Yield: 87%.

EXAMPLE 11

2-n-Butyl-4-(N-methylaminomethyl)4,5,6,7-tetrahydrobenzo[d]thiazole and its hydrochloride (I; R=nC$_4$H$_9$; R'=CH$_3$; substitution at 4-position)

(1)
2-n-Butyl-4-ethoxycarbonyl-4,5,6,7-tetrahydrobenzo[d]thiazole (III)

The compound is obtained by action of thiovaleramide on 2-bromo-6-ethoxycarbonyl-cyclohexanone according to the procedure described in Example 1. B.p.$_{0.5}$=116°–128° C. Yield: 28%.

(2)
2-n-Butyl-4-hydroxymethyl-4,5,6,7-tetrahydrobenzo[d]thiazole (IV)

The compound is prepared by reduction of the above derivative (III), with AlLiH$_4$ in ether at room temperature. B.p.$_{0.6}$=130°–132° C. Yield:48%.

(3)
2-n-Butyl-4-tosyloxymethyl-4,5,6,7-tetrahydrobenzo[d]thiazole (V)

The compound is prepared by action of p-toluenesulfonyl chloride on the above derivative (IV), according to the procedure described in Example 1. The product is an undistillable oil which is used crude for the subsequent reactions.

(4)
2-n-Butyl-4-(N-methylaminomethyl)-4,5,6,7-tetrahydrobenzo[d]thiazole and its hydrochloride (I; R=nC$_4$H$_9$; R'=CH$_3$)

The compound is prepared by action of methylamine in methanol solution on the above tosylate (V), in an autoclave at 90° C. B.p.$_{0.5}$=118°–120° C. Yield: 74%.

The base is converted to the hydrochloride with HCl in anhydrous ether. M.p.=128° C. Yield: 70%

EXAMPLE 12

2-n-Butyl-5-(N-methylaminomethyl)-4,5,6,7-tetrahydrobenzo[d]thiazole and its hydrochloride (I; R=nC$_4$H$_9$; R'=CH$_3$; substitution at 5-position)

(1)
2-n-Butyl-5-ethoxycarbonyl-4,5,6,7-tetrahydrobenzo[d]thiazole (III)

The compound is obtained by action of thiovaleramide on 2-bromo-5-ethoxycarbonyl-cyclohexanone within dimethyl formamide at room temperature. B.p.$_{0.5}$=140°–142° C. Yield: 56%.

(2)
2-n-Butyl-5-hydroxymethyl-4,5,6,7-tetrahydrobenzo[d]thiazole (IV)

The compound is prepared by reduction of the above derivative (III) with AlLiH$_4$ in ether at room temperature. B.p.$_{0.15}$=138°–142° C. Yield: 89%.

(3)
2-n-Butyl-5-tosyloxymethyl-4,5,6,7-tetrahydrobenzo[d]thiazole (V)

The compound is prepared by action of p-toluenesulfonyl chloride on the above derivative (IV), according to the procedure described in Example 1. It is obtained as an undistillable oil which is used crude for the subsequent reactions.

(4)
2-n-Butyl-5-(N-methylaminomethyl)-4,5,6,7-benzo[d]-thiazole and its hydrochloride (I; R=nC4H9; R'=CH3)

The compound is obtained by action of methylamine in methanol solution on the above tosylate (V), in an autoclave at 90° C. B.p.=122°–124° C. Yield: 72%.

The base is converted to the hydrochloride with HCl in anhydrous ethanol. M.p.=169°–171° C. Yield: 100%.

EXAMPLE 13
2-Isopropyl-5-(N-methylaminomethyl)-4,5,6,7-tetrahydrobenzo[d]thiazole and its hydrochloride (I; R=iC3H7; R'=CH3; substitution at 5-position)

(1)
2-Isopropyl-5-ethoxycarbonyl-4,5,6,7-tetrahydrobenzo[d]thiazole (III)

The compound is obtained by action of thioisobutyramide on 2-bromo-6-ethoxycarbonyl-cyclohexanone within dimethylformamide, at room temperature. B.p.$_{0.05}$=109°–111° C. Yield: 50%.

(2)
2-isopropyl-5-hydroxymethyl-4,5,6,7-tetrahydrobenzo[d]thiazole (IV)

The compound is prepared by reduction of the above derivative (III) with AlLiH4 in ether at room temperature. B.p.$_{0.1}$=122°–126° C. Yield: 83%.

(3)
2-Isopropyl-5-tosyloxymethyl-4,5,6,7-tetrahydrobenzo[d]thiazole (V)

The compound is prepared by action of p-toluenesulfonyl chloride on the above derivative (IV), according to the procedure described in Example 1. M.p.=82°–83° C. Yield: 71%

(4)
2-Isopropyl-5-(N-methylaminomethyl)-4,5,6,7-tetrahydrobenzo[d]thiazole and its hydrochloride (I; R=iC3H7; R'=CH3)

The compound is prepared by action of methylamine in methanol solution on the above tosylate (V), in an autoclave at 90° C. B.p.=108°–109° C. Yield: 85%.

The base is converted to the hydrochloride with HCl in anhydrous ether. M.p.=177° C. Yield: 98%.

Other Examples of compounds of the formula (I) prepared in an analogous manner are tabulated in following Table I.

TABLE I

| Ex. | Formula | Designation | Physical characteristics | Yield % |
|-----|---------|-------------|--------------------------|---------|
| 14 | NH2CH2— (tetrahydrobenzothiazole, 2-H) | 5-aminomethyl-4,5,6,7-tetrahydro-benzo[d]thiazole | base bp$_{0.7}$ = 116–118° C.<br>hydro-chloride M.p. = 119–201° C. | 68<br>95 |
| 15 | NH2CH2— (tetrahydrobenzothiazole, 2-CH3) | 2-methyl-5-aminomethyl-4,5,6,7-tetrahydro-benzo[d]thiazole | base bp$_{0.5}$ = 115–125° C.<br>hydro-chloride M.p. = 262–263° C. | 48<br>100 |
| 16 | CH3NHCH2— (tetrahydrobenzothiazole, 2-H, 6-position) | 6-(N—methylaminomethyl)-4,5,6,7-tetrahydro-benzo[d]thiazole | base bp$_{0.3}$ = 98–102° C.<br>hydro-chloride M.p. = 225–227° C. | 51<br>77 |
| 17 | NH2CH2— (tetrahydrobenzothiazole, 2-CH3, 6-position) | 2-methyl-6-aminomethyl-4,5,6,7-tetrahydro-benzo[d]thiazole | base bp$_{0.5}$ = 120–130° C.<br>hydro-chloride M.p. = 206–207° C. | 70<br>72 |
| 18 | nC4H9NH—CH2— (tetrahydrobenzothiazole, 2-CH3, 4-position) | 2-methyl-4-(N—n-butylamino-methyl)-4,5,6,7-tetrahydro-benzo[d]thiazole | base bp$_{0.6}$ = 118–122° C.<br>hydro-chloride M.p. = 132° C. | 76<br>94 |
| 19 | iC3H7NH—CH2— (tetrahydrobenzothiazole, 2-CH3, 5-position) | 2-methyl-5-(N—isopropylamino-methyl)-4,5,6,7-tetrahydro-benzo[d]thiazole | base bp$_{0.2}$ = 102–106° C.<br>hydro-chloride M.p. = 204–205° C. | 82<br>100 |
| 20 | nC4H9NH—CH2— (tetrahydrobenzothiazole, 2-CH3, 5-position) | 2-methyl-5-(N—n-butylamino-methyl-4,5,6,7-tetrahydro-benzo[d]thiazole | base bp$_{0.1}$ = 112–118° C.<br>hydro-chloride M.p. = 245° C. | 81<br>100 |

The compounds of the formula (I) and their pharmaceutically acceptable acid addition salts possess useful pharmacological properties, particularly on the cardiovascular system. Thus, they have an effect, which is substantial with some of them, on the increase of the blood rate of flow for the perfusion of the limbs.

This activity on the cardiovascular system was demonstrated by means of a conventional test in dogs comprising determining the rate of flow of the femoral arteries. Thus, with some of the compounds, there was noted an increase of the arterial rate of flow from as low a dosage as 0.1–0.5 mg/kg i.v.

In addition, in the case of an acute occlusion of the femoral artery, there was noted a marked decrease of the resistance of the collateral arteries with the compounds of Examples 6 and 11, without substantially affecting the systemic blood pressure, not the tissue perfusion pressure.

Most of the compounds of the formula (I) have low toxicity, as is apparent from following Table II in which are given the $LD_{50}$ per os and i.p. in mice.

TABLE II

| | Acute toxicity in mice | |
|---|---|---|
| Example no | Oral route $LD_{50}$ (mg/kg) | Intraperitoneal route $LD_{50}$ (mg/kg) |
| 1 | >200 | 140 |
| 2 | >200 | ≧200 |
| 3 | >200 | — |
| 5 | >200 | >200 |
| 6 | >200 | — |
| 7 | >200 | >200 |
| 8 | >200 | >200 |
| 9 | >200 | 120 |
| 10 | >200 | 190 |
| 11 | ≧200 | 58 |
| 12 | >200 | 140 |
| 13 | >200 | 140 |
| 14 | ≧200 | >200 |
| 15 | >200 | >200 |
| 16 | 170 | 75 |
| 17 | >200 | >200 |
| 18 | >200 | 58 |
| 19 | >200 | >200 |
| 20 | 145 | 58 |

The compounds of the formula (I) and their pharmaceutically acceptable acid addition salts are therapeutically useful in the treatment of circulatory insufficiencies of different origins.

In that respect, the compounds of Example 6 and 11 appear to be particularly useful.

The compounds may be administered to humans by the oral, rectal or parenteral routes, as the free base or in salt form, in aqueous solution or as solutions in other pharmaceutically acceptable solvents, as suspensions or in crystalline form. The different formulations may contain 10–500 mg active ingredient per unit dose and the daily dosage regimen in humans may vary from 20 mg to 2 g. depending on the therapeutic applications contemplated.

Having now described our invention what we claim as new and desire to secure by Letters Patent is:

1. A therapeutic composition increasing the blood rate of flow containing an amount, effective for increasing the blood rate of flow, of a compound selected from the compounds of the formula:

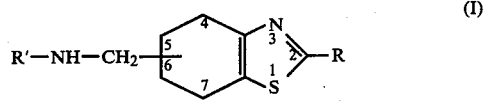

in which:
the group R′—NH—CH₂— is in the 4, 5 or 6 position,
R is selected from hydrogen and $C_{1-6}$ alkyl,
R′ is selected from hydrogen and $C_{1-6}$ alkyl, and a pharmaceutically acceptable acid addition salt thereof, and a therapeutically acceptable excipient.

2. A therapeutic composition as claimed in claim 1, in which said compund is 2-methyl-5-(N-methylaminomethyl)-4,5,6,7-tetrahydrobenzo[d]thiazole or a pharmaceutically acceptable acid addition salt thereof.

3. A therapeutic composition as claimed in claim 1, in which said compound is 2-n-butyl-4-(N-methylaminomethyl)-4,5,6,7-tetrahydrobenzo[d]-thiazole or a pharmaceutically acceptable acid addition salt thereof.

4. A process for the treatment of circulatory insufficiencies which comprises administering to a human in need thereof an amount, effective for increasing the blood rate of flow, of a compound selected from the compounds of the formula:

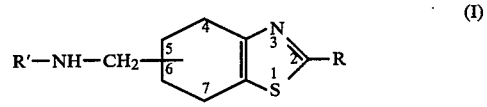

in which:
the group R′—NH—CH₂— is in the 4, 5 or 6 position,
R is selected from hydrogen and $C_{1-6}$ alkyl,
R′ is selected from hydrogen and $C_{1-6}$ alkyl,
and a pharmaceutically acceptable acid addition salt thereof.

5. A process as claimed in claim 4, in which said compound is 2-methyl-5-(N-methylaminomethyl)-4,5,6,7-tetrahydrobenzo[d]thiazole or a pharmaceutically acceptable acid addition salt thereof.

6. A process as claimed in claim 4, in which said compound is 2-n-butyl-4-(N-methylaminomethyl)-4,5,6,7-tetrahydrobenzo[d]thiazole or a pharmaceutically acceptable acid addition salt thereof.

* * * * *